(12) United States Patent
Mirbeik-Sabzevari et al.

(10) Patent No.: US 12,332,335 B2
(45) Date of Patent: Jun. 17, 2025

(54) SYNTHETIC ULTRAWIDEBAND INTEGRATED MILLIMETER-WAVE IMAGER

(71) Applicant: THE TRUSTEES OF THE STEVENS INSTITUTE OF TECHNOLOGY, Hoboken, NJ (US)

(72) Inventors: Amir Mirbeik-Sabzevari, Hoboken, NJ (US); Negar Tavassolian, Hoboken, NJ (US)

(73) Assignee: The Trustees of the Stevens Institute of Technology, Hobokan, NJ (US)

( * ) Notice: Subject to any disclaimer, the term of this patent is extended or adjusted under 35 U.S.C. 154(b) by 246 days.

(21) Appl. No.: 17/838,033

(22) Filed: Jun. 10, 2022

(65) Prior Publication Data

US 2022/0397660 A1    Dec. 15, 2022

Related U.S. Application Data

(60) Provisional application No. 63/209,244, filed on Jun. 10, 2021.

(51) Int. Cl.
G01S 13/90    (2006.01)
A61B 5/00    (2006.01)
(Continued)

(52) U.S. Cl.
CPC ............ *G01S 13/0209* (2013.01); *A61B 5/05* (2013.01); *A61B 5/444* (2013.01); *G01S 7/03* (2013.01);
(Continued)

(58) Field of Classification Search
None
See application file for complete search history.

(56) References Cited

U.S. PATENT DOCUMENTS 4,680,538 A     7/1987  Dalman
5,146,616 A  *  9/1992  Tang ................... G01S 13/0209
                                                            455/119
(Continued)

FOREIGN PATENT DOCUMENTS

WO    WO-2020219954 A1 * 10/2020 ........... G01S 13/325

OTHER PUBLICATIONS

P. Chen and A. Babakhani, "A 30 GHz impulse radiator with on-chip antennas for high-resolution 3D imaging," in Proc. IEEE Radio Wireless Symp. (RWS), Jan. 2015, pp. 32-34.
(Continued)

*Primary Examiner* — Vladimir Magloire
*Assistant Examiner* — Brandon James Henson
(74) *Attorney, Agent, or Firm* — Clark Hill PLC; Ralph W. Selitto; John K. Kim (57) ABSTRACT

The present disclosure relates to an apparatus and method for synthetically making an ultra-wide imaging bandwidth in millimeter-wave frequencies, resulting in improved image resolutions to values previously unattained. The synthetic approach sums up a number of available sub-bands to build an unavailable ultra-wideband system. Each sub-band contains a transceiver unit which is optimized for operation within that specific sub-band. The number and position of the sub-bands can be adjusted to cover any frequency range as required for the specific application.

21 Claims, 8 Drawing Sheets

(51) Int. Cl.
    *A61B 5/05*     (2021.01)
    *G01S 7/03*     (2006.01)
    *G01S 13/02*     (2006.01)
    *G01S 13/34*     (2006.01)

(52) U.S. Cl.
    CPC ......... *G01S 13/347* (2013.01); *G01S 13/9011* (2013.01)

(56) References Cited

U.S. PATENT DOCUMENTS

| | | | |
|---|---|---|---|
| 5,945,940 | A | 8/1999 | Cuomo |
| 6,373,432 | B1 | 4/2002 | Rabinowitz |
| 6,466,958 | B1 | 10/2002 | Van Wechel |
| 9,265,438 | B2 | 2/2016 | Weinstein |
| 9,372,256 | B2 | 6/2016 | Mohamadi |
| 10,976,428 | B2 | 4/2021 | Tavassolian |
| 2002/0140616 | A1 | 10/2002 | Kanamaluru |
| 2003/0138060 | A1 | 7/2003 | Alcouffe |
| 2004/0254457 | A1* | 12/2004 | van der Weide ........ A61B 5/05 600/430 |
| 2004/0264626 | A1 | 12/2004 | Besson |
| 2005/0270231 | A1 | 12/2005 | Small |
| 2009/0289833 | A1 | 11/2009 | Johnson |
| 2010/0225520 | A1 | 9/2010 | Mohamadi |
| 2013/0307716 | A1 | 11/2013 | Mohamadi |
| 2016/0124069 | A1 | 5/2016 | Sendonaris |
| 2016/0131754 | A1 | 5/2016 | Cornic |
| 2016/0178730 | A1 | 6/2016 | Trotta |
| 2016/0377728 | A1 | 12/2016 | Kreienkamp |
| 2018/0252807 | A1* | 9/2018 | Fox ....................... G01S 13/904 |
| 2020/0158861 | A1* | 5/2020 | Cattle ................... G01S 13/345 |
| 2021/0255314 | A1 | 8/2021 | Tavassolian |

OTHER PUBLICATIONS

A. Arbabian, S. Callender, S. Kang, M. Rangwala, and A. M. Niknejad, "A 94 GHz mm-wave-to-baseband pulsed-radar transceiver with applications in imaging and gesture recognition," IEEE J. Solid-State Circuits, vol. 48, No. 4, pp. 1055-1071, Apr. 2013.

A. Mirbeik-Sabzevari, S. Li, E. Garay, H. Nguyen, H. Wang and N. Tavassolian, "Synthetic Ultra-High-Resolution Millimeter-Wave Imaging for Skin Cancer Detection," IEEE Transactions on Biomedical Engineering, vol. 66, No. 1, pp. 61-71, Jan. 2019.

A. Mostajeran et al., "A High-Resolution 220-GHz Ultra-Wideband Fully Integrated ISAR Imaging System," IEEE Transactions on Microwave Theory and Techniques, vol. 67, No. 1, pp. 429-442, Jan. 2019.

A. Tang et al., "A 144 GHz 0.76 cm-resolution sub-carrier SAR phase radar for 3D imaging in 65 nm CMOS," in Proc. IEEE Int. Solid-State Circuits Conf., San Francisco, CA, USA, Feb. 2012, pp. 264-266.

D. Lin, A. Trasser and H. Schumacher, "Low power, fully differential SiGe IR-UWB transmitter and correlation receiver ICs," in 2011 IEEE Radio Frequency Integrated Circuits Symposium, Baltimore, MD, 2011, pp. 1-4.

Mirbeik-Sabzevari et al., "Ultra-Wideband Millimeter-Wave Dielectric Characteristics of Freshly-Excised Normal and Malignant Human Skin Tissues," IEEE Transactions on Biomedical Engineering, vol. 65, No. 6, Jun. 2018.

Mirbeik-Sabzevari et al., "Characterization and Validation of the Slim-Form Open-Ended Coaxial Probe for the Dielectric Characterization of Biological Tissues at Millimeter-Wave Frequencies," IEEE Microwave and Components Letters, vol. 28, No. 1, Jan. 2018.

Mirbeik-Sabzevari et al., "W-Band Micromachined Antipodal Vivaldi Antenna Using SIW and CPW Structures," IEEE Transactions on Antennas and Propagation, vol. 66, Issue 11, Nov. 2018.

* cited by examiner

SYNTHETIC ULTRAWIDEBAND INTEGRATED MILLIMETER-WAVE IMAGER

CROSS-REFERENCE TO RELATED APPLICATION

This application claims priority to U.S. Provisional Patent Application No. 63/209,244, filed Jun. 10, 2021, the entire disclosure of which is incorporated herein by reference for all purposes. This application also relates to the subject matter disclosed in U.S. patent application Ser. No. 17/228,515, filed Apr. 12, 2021, which is a continuation-in-part of U.S. patent application Ser. No. 16/275,149, filed Feb. 13, 2019, now U.S. Pat. No. 10,976,428, which is a continuation-in-part of U.S. patent application Ser. No. 15/895,991, filed Feb. 13, 2018, which claims priority to U.S. Provisional Patent Application Ser. No. 62/458,890, filed Feb. 14, 2017 and to U.S. Provisional Patent Application Ser. No. 62/630,167, filed Feb. 13, 2018, the entire disclosures of each of the foregoing applications being incorporated herein by reference for all purposes.

STATEMENT REGARDING FEDERALLY SPONSORED RESEARCH

This invention was made with government support under Grant Nos. 1554402 and 1919194 awarded by the National Science Foundation. The government has certain rights in the invention.

FIELD OF THE INVENTION

The present invention relates to millimeter-wave imaging, particularly for biomedical applications.

BACKGROUND OF THE INVENTION

Millimeter-wave imaging is a relatively mature and low-cost imaging technology. However, it has only been applied in military and commercial settings thus far. Despite the various potential advantages of this technology in the biomedical imaging context, such as high image contrasts and suitable penetration depths, it has not been applied in any such applications.

Millimeter-wave imaging is generally performed using wideband techniques (either in frequency or time domain), wherein the image resolution is directly proportional to the bandwidth of the system. While some silicon-based millimeter-wave imaging systems for biomedical applications have been developed, with the goal of achieving high resolutions, large image ranges, and short acquisition times, there exists no imaging chip with the capability of providing sufficient resolutions for the visualization of tissues.

There has been a great amount of interest in the generation and radiation of ultra-wideband electromagnetic waves in the millimeter-wave regime. Ultra-wideband radiation can be used in broadband spectroscopy, 3-D imaging, and high-speed wireless communications. The absorption profiles and molecular structure alterations turn this region of the spectrum into a unique platform for tissue spectroscopy. Higher spatial resolutions compared to lower-frequency, and the nonionizing nature compared to higher-frequency waves (e.g. X-ray), add to the exclusive features of millimeter waves for medical imaging applications.

This invention addresses the low image resolutions achieved using current technology by providing significant improvements in the resolution of acquired images. This improvement is achieved by synthesizing an unprecedented ultra-wide imaging bandwidth.

SUMMARY OF THE INVENTION

In view of the foregoing background, an apparatus and method are provided in which several millimeter-wave sub-bands are processed and combined for an ultra-wideband performance, while the sub-bands are successive and disjointed.

In a preferred embodiment, the integrated imaging system is arranged so that the required ultra-wide bandwidth in the millimeter-wave frequencies is divided into a number of sub-bands, wherein each sub-band separately embraces a sub-band imaging element (transceiver). In another preferred embodiment, the sub-band responses are combined and processed to synthesize an ultra-wideband signal.

As a result of the present invention, an integrated imaging system with an unprecedented ultra-wide bandwidth in the millimeter-wave frequencies is provided for use with tissue imaging and diagnostic applications. The immediate application of the system is in the early-stage detection of skin cancer. The imaging system can be employed as a reliable and harmless device to help dermatologists with more efficient diagnosis and management of skin cancer. In addition to being used for tissue imaging and biomedical applications, the present invention will allow for millimeter-wave imaging to be used for such applications as dental care (cavity detection) and non-destructive testing (NDT).

In an embodiment, the above-mentioned millimeter-wave imaging system can be translated into a hand-held, point-of-care imaging device. Such a device would apply the synthetic ultra-wideband imaging approach to the transmitting and receiving circuitries as well the antennas. This enables the imaging system to be integrated in a single framework, resulting in a compact (handheld) and real-time imager at a very low manufacturing cost. This would make the inventive technology comparable in cost to dermatoscopic imaging—which is a common skin examination tool that consists of a magnifying lens—facilitating its widespread use and application. The medical imaging industry in particular would greatly benefit from such integration procedures and the associated cost reductions.

BRIEF DESCRIPTION OF THE DRAWINGS

For a more complete understanding of the present invention, reference is made to the following detailed description of an embodiment considered in conjunction with the accompanying drawings, in which.

DETAILED DESCRIPTION OF THE EXEMPLARY EMBODIMENT

The following disclosure is presented to provide an illustration of the general principles of the present invention and is not meant to limit, in any way, the inventive concepts contained herein. Moreover, the particular features described in this section can be used in combination with the other described features in each of the multitude of possible permutations and combinations contained herein.

All terms defined herein should be afforded their broadest possible interpretation, including any implied meanings as dictated by a reading of the specification as well as any words that a person having skill in the art and/or a dictionary, treatise, or similar authority would assign thereto.

Further, it should be noted that, as recited herein, the singular forms "a", "an", "the", and "one" include the plural referents unless otherwise stated. Additionally, the terms "comprises" and "comprising" when used herein specify that certain features are present in that embodiment, however, this phrase should not be interpreted to preclude the presence or addition of additional steps, operations, features, components, and/or groups thereof.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The present invention relates to imaging systems with ultra-wide bandwidths in the millimeter-wave frequencies for tissue imaging and diagnostic applications, and methods for synthesizing same. A main advantage of the systems is their application in the early-stage detection of skin cancer.

Figure 1:
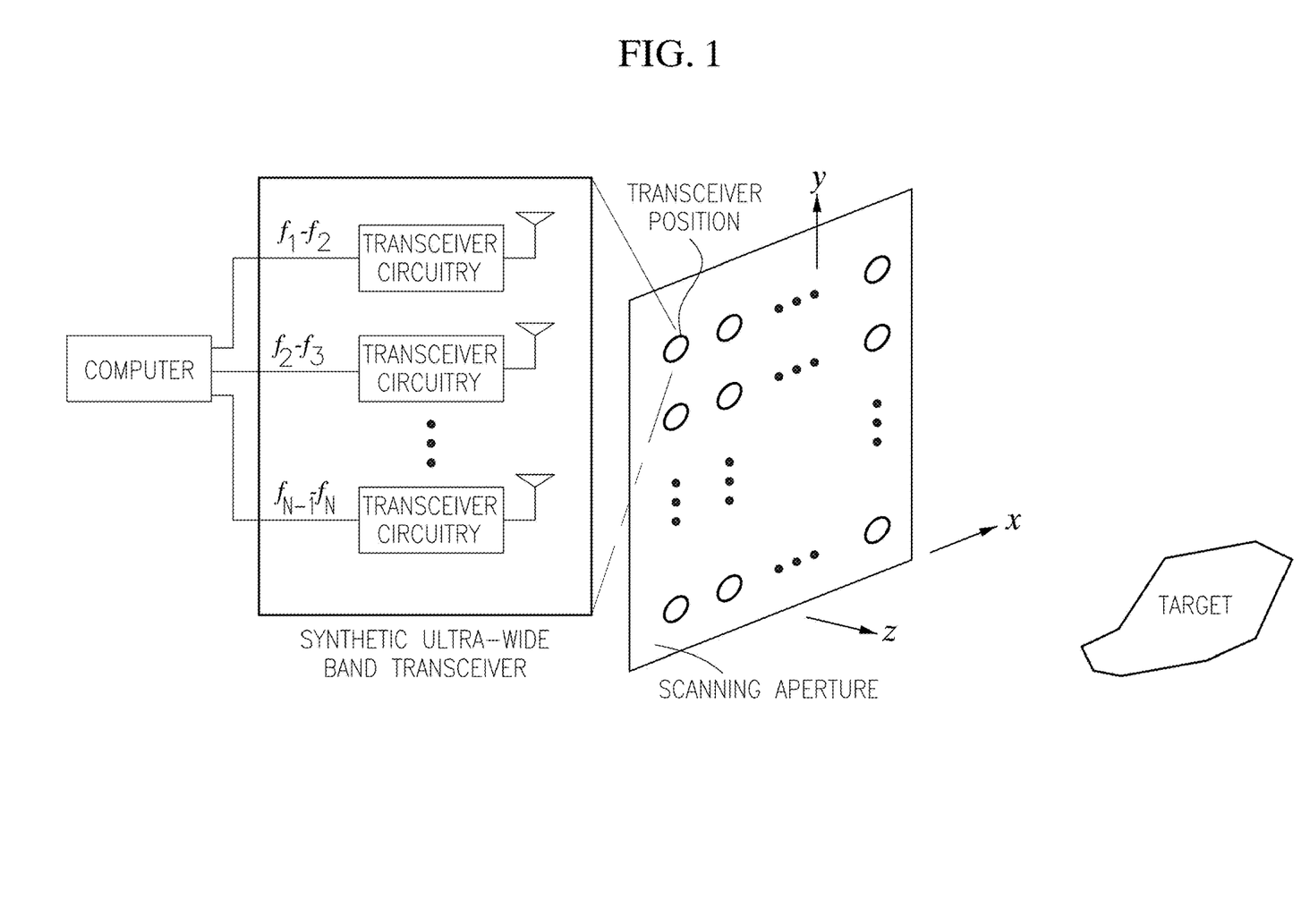
FIG. 1 is a millimeter-wave imaging system in accordance with an embodiment of the present invention.

The present invention is described herein with reference to FIGS. 1-7, which figures illustrate, but do not fully encompass, the invention. The main component of the millimeter-wave imaging system is an array of transceivers which generates and sends millimeter-wave signals to a target of which the image is to be formed, and subsequently picks up (collects) the reflection signals from the target (FIG. 1). Each transceiver element can operate both as a transmitter and a receiver. The location of receiving elements, which collect the scattered signals from the target may be the same or different than the location of transmitting elements. In one embodiment, the transceiver circuitry generates, as well as records, signals over a specific range of millimeter-wave frequencies. After a signal is generated by the circuitry, it is radiated as an electromagnetic wave through a transmitting antenna to the space containing the target. The reflected waves from the target are then captured by a receiving antenna connected to the circuitry, wherein the incoming backscattered waves are recorded by a millimeter-wave detector. In certain embodiments, the data collection can be performed either by scanning a transmitting and receiving elements over a rectilinear planar aperture (i.e. monostatic imaging) or by electronically switching on/off an array comprising multiple transceivers (i.e. multi-static imaging). For the latter, the signal is radiated from one antenna to the target and reflections from the target are collected by all of the antennas in the array. This process is repeated until all antenna elements have radiated their signals. In this case, the transmitting/receiving circuitry consists of a switching network, which selects transmitting/receiving pairs successively for generation and recording of the signals.

Figure 2:
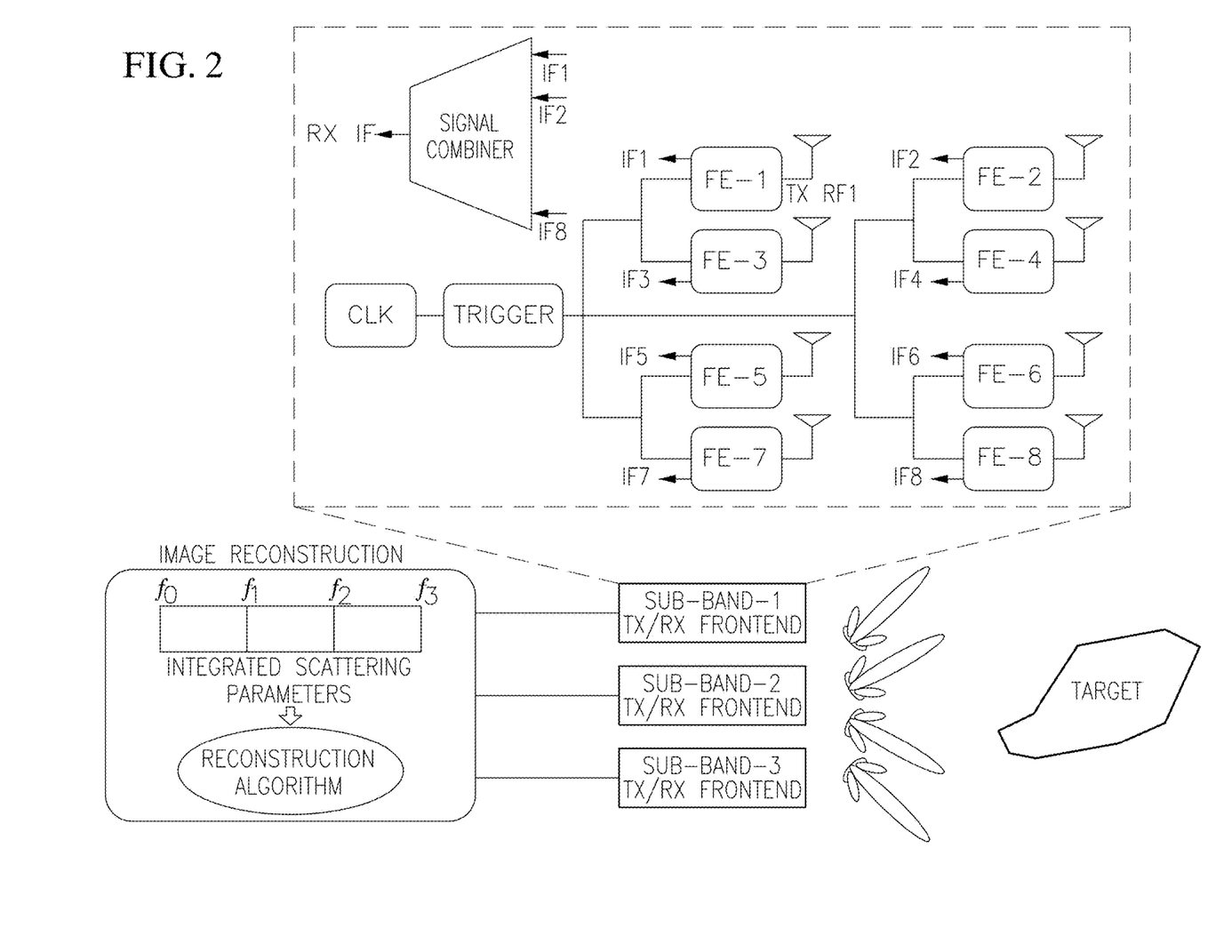
FIG. 2 is a schematic diagram of a synthetic ultra-wideband millimeter-wave imager integrated with phased-array antennas in accordance with an embodiment of the present invention.

In another embodiment, electronic beam-forming is used to scan the target region. Beam-forming allows an antenna system comprising a number of individual antennas to control the direction of the beam by changing the phase and amplitude of the input signals. The block diagram of a phased-array transceiver consisting of 8 (4×2) elements is shown in FIG. 2. Each element is equipped with a programmable delay (or phase shifter) line that controls the individual timing of radiation to perform low-loss signal distribution and coherent combination of broadband pulses of all elements. On-chip or off-chip antennas can be used for radiation and collection purposes. On-chip antennas are used to eliminate the power loss and phase distortion caused by connections to off-chip antennas. In one embodiment, each antenna is used for both radiation and reception of the waves towards and from the target, respectively, eliminating the need to provide two separate antennas (i.e., one for transmitting signals and the other one for receiving returning signals) functions and thereby reducing the overall size and/or power consumption of the associated imaging element, or device as a whole.

Figure 3:
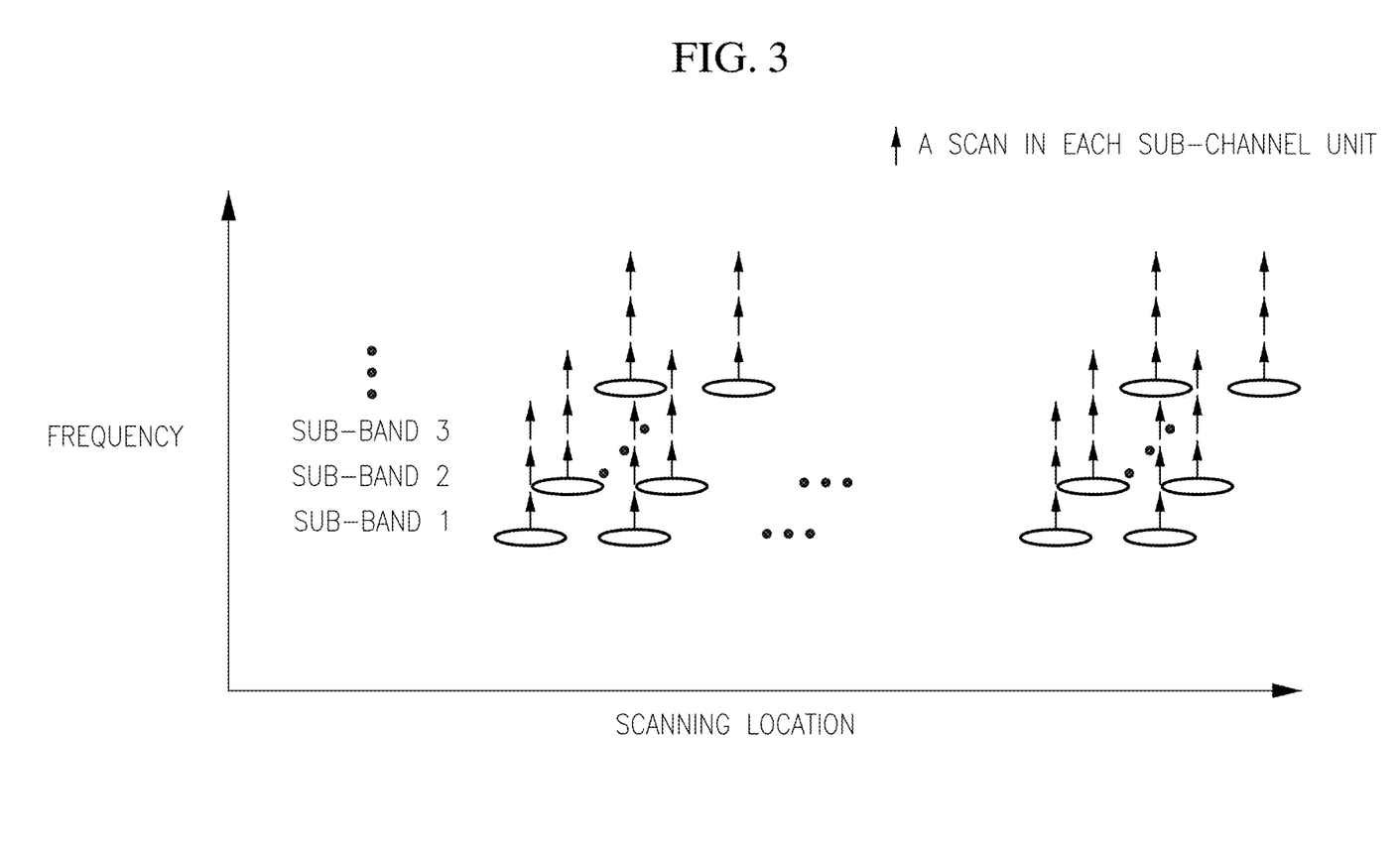
FIG. 3 is a graphical representation of a scan mechanism using the synthetic ultra-wideband approach according to an embodiment of the present invention.

Generally, an embodiment of the present invention encompasses a method by which an ultra-wide imaging frequency range ($f_1$ to $f_N$) is realized by the integration of several disjointed adjacent sub-bands. Each sub-band corresponds to a transceiver unit which operates within that specific sub-band. At each scanning step, all the sub-band transceivers which operate at a specific sub-band are placed at specified positions in front of the target and transmit (radiate) the signals across that specific sub-band to the target (FIG. 3). For each transmitting radiation, the sub-band backscattered signals are recorded for all transceiver locations by using a millimeter-wave signal detector in a similar manner as described earlier. After all transceiver pairs have been selected as transceiver/receiver elements, the above process is repeated for all imaging sub-bands.

Figure 4:
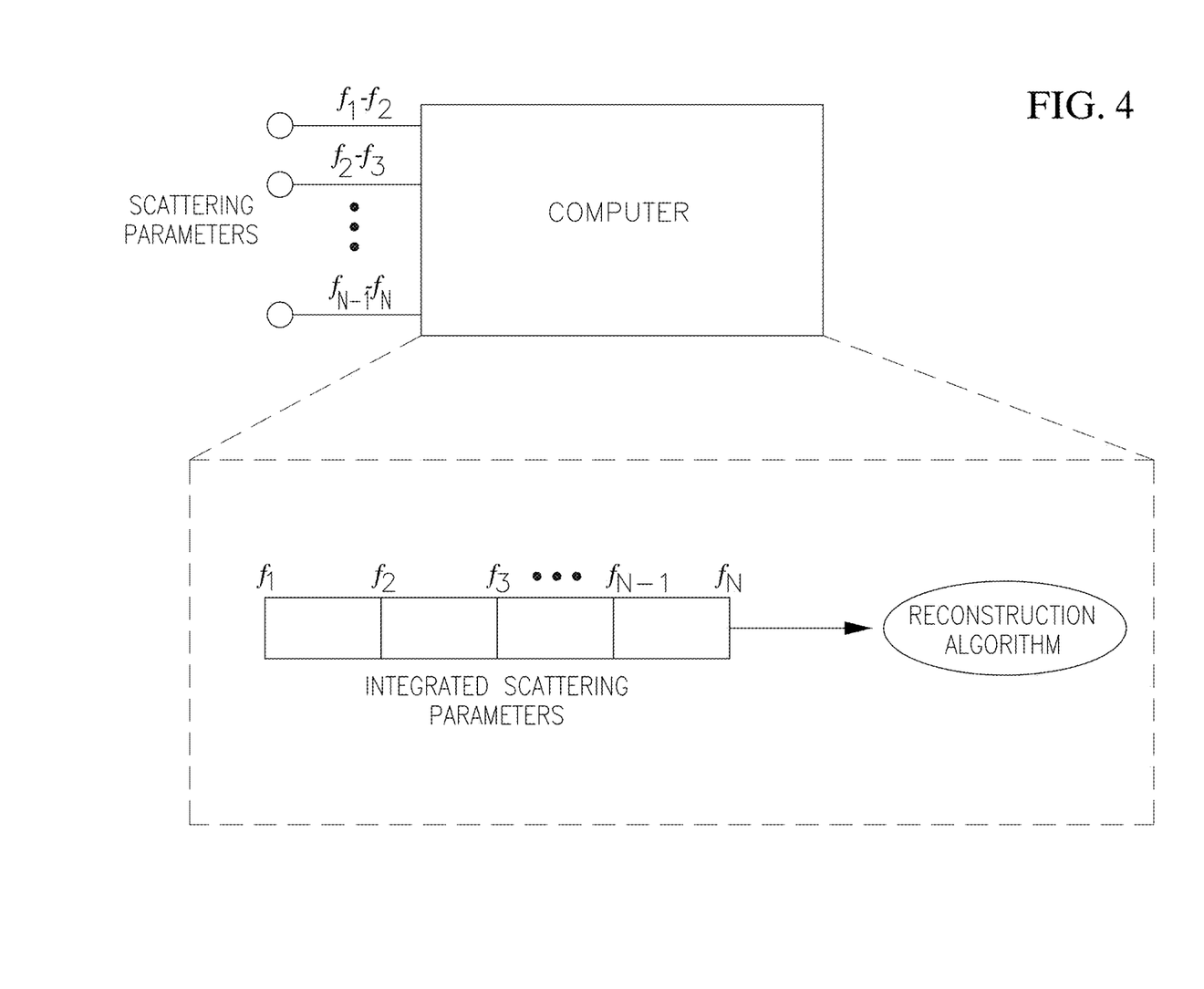
FIG. 4 is a schematic diagram of an embodiment of a method according to the present invention for an integration scheme according to an embodiment of the present invention.

Another embodiment of the present invention encompasses a method by which the sub-band backscattered responses for each transceiver location are combined to synthesize an integrated signal. This is performed by sequentially arranging the sub-band signals over the frequency domain to cover the whole ultra-wideband range of $f_1$ to $f_N$. For each transceiver location, the sub-band scattering parameters are recorded for all transceiver pairs. The collected sub-band scattering parameters are imported into a computer or a signal processor where a signal integration scheme is used to combine the sub-bands and generate an integrated signal (FIG. 4). The integrated signal is used as a transfer function to calculate the pulse response from the incident pulse in the frequency domain. Pulse responses are subsequently converted to time domain by applying an Inverse Fourier Transform (IFT) operation. In one embodiment, the image of the target is formed using a reflectivity function, defined as the ratio of the reflected to incident fields. A suitable reconstruction algorithm (for example the standard delay-and-sum (DAS) or delay-multiply-and-sum (DMAS) algorithms) will be applied to the pulse responses in the time domain to form a 3D image of the target. The image reconstruction algorithm is also executed using a computer or a signal processor. The approach is versatile, as the number and position of the sub-bands can be adjusted to cover any frequency range as required for the specific application. The technique can be applied to mono-static as well as multi-static imaging setups. Alternatively, it can be implemented via beam-steering (i.e., phased arrays). For instance, in such embodiments, multiple transmitting elements may be active simultaneously. In one embodiment, the synthetic-aperture radar (SAR) method may be used for creating three-dimensional reconstructions of objects. SAR uses a two-dimensional (2D) array of antennas to scan the target region and collect data. However, scanning over a 2D aperture plane increases the size of the system and is not a reasonable approach in silicon-based systems. Phased-array beam-forming and beam-steering capabilities increase the range and improve the signal-to-noise ratio (SNR).

An alternate embodiment of the present invention will now be described. Unless stated otherwise, the features described hereinabove are applicable to this and other alternate embodiments. In such an embodiment, each sub-band corresponds to transmitting and receiving units which operate within that specific sub-band. The present imaging system can be integrated on a single chip for biomedical imaging. Two different techniques have been traditionally used to produce wideband signals in the millimeter-wave regime and can be used in combination with one or more embodiments of the present invention. The first technique is based on modulating voltage-controlled oscillators (VCO). In frequency-modulated continuous-wave (FMCW) imaging chips, the intermediate frequency (IF) is typically on the order of tens to hundreds of kilohertz. This frequency range simplifies the design of the baseband circuit and the data processing procedure. However, FMCW systems require wide tuning ranges which is challenging to be implemented on silicon. At high frequencies, on-chip varactors become lossy, limiting their tuning ranges. In addition, the direct coupling between Tx and Rx due to the continuous radiation of signals in FMCW systems generates a strong in-band interference.

The second technique for producing ultra-wideband signals relies on an oscillator followed by a fast switch which turns the oscillating signal to ON and OFF states and hence produces a pulse. Pulse-based imaging chips require fast and low-loss switches with high isolation levels. Another drawback of these systems is the challenge in baseband design and data processing due to the large baseband bandwidth. However, these systems have three main advantages compared to continuous-wave imaging chips. First, pulse generators have larger relative bandwidths compared to continuous-wave radiators, resulting in higher image resolutions. Second, the leakage from Tx to Rx is much less since unlike continuous-wave imaging chips, pulsed oscillators frequently switch between ON and OFF states by a trigger signal and do not radiate continuously. Third, the power consumption of pulse generators can be controlled by adjusting the repetition rate of the pulses.

One implementation of such a chip can be done through BiCMOS technology, which is an effective platform for low-power millimeter-wave transceiver systems. In an embodiment, the chip operates with a state-of-the-art bandwidth of 100 GHz. In an exemplary embodiment, the ultra-wide imaging bandwidth of 100 GHz is realized by the integration of three adjacent, disjointed frequency sub-bands. In one embodiment, the number of bands can be scaled up, and the bandwidth may be further divided. To this end, three integrated pulse generators have been developed. Such a development is the first step towards the realization of a fully-integrated ultra-high-resolution imaging chip for biomedical applications. The use of pulse generators further enables miniaturization when compared to other implementations (e.g., Vector Network Analyzers).

The pulse generators can be designed in Global Foundry 130-nm SiGe BiCMOS process technology and can be configured to produce pulses with frequency ranges of 10-40-GHz, 40-75-GHz, and 75-110-GHz respectively. The three sub-band pulse generators possess a similar differential pulsed VCO configuration with the highest average power consumption of 40 mW.

Figure 5:
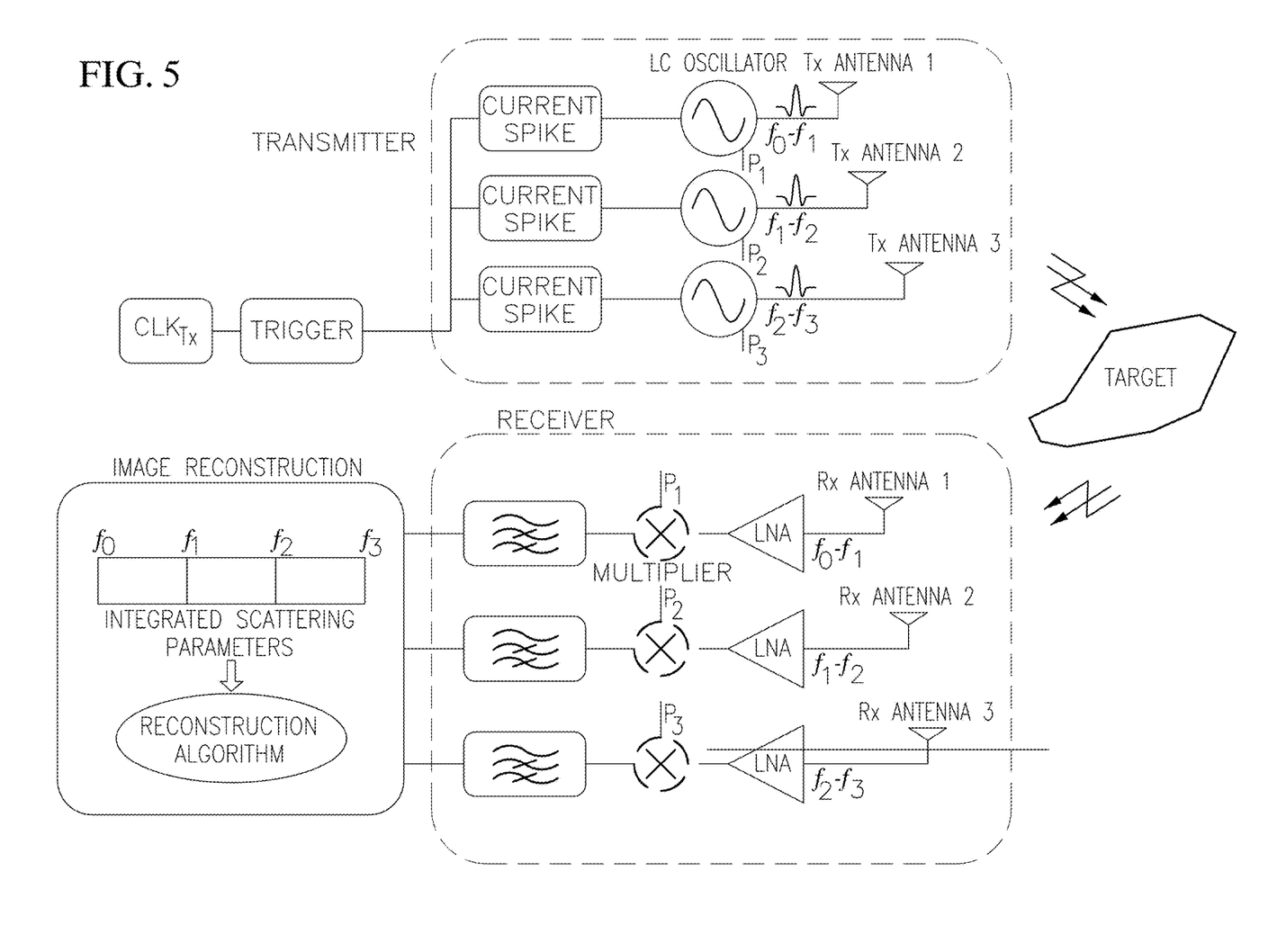
FIG. 5 is a schematic diagram of transmitter and receiving elements in accordance with an embodiment of the present invention.

The schematic of a proposed synthetic ultra-wideband imaging chip in accordance with an embodiment of the present invention is shown in FIG. 5. FIG. 5 shows a schematic diagram of the imaging transmitter (top) and imaging receiver (bottom) for the three sub-bands mentioned hereinabove. As seen in this figure, a separate imaging element (i.e., a radiator including a pulse generator and an antenna) is used for each sub-band. Each radiator operates only within its specific sub-band. In the imaging setup, at each scanning location the sub-band radiators transmit their signals in their respective frequency ranges. Similarly, on the receiving side, three sub-band antennas receive the reflected waves from the target over their corresponding frequencies. In one embodiment, the transmitting and receiving antennas on the radiators of the respective imaging elements are formed as a single antenna. To improve performance, the received sub-band signals can be amplified and mixed with the generated pulses from the sub-band pulse generators by three sub-band mixers. Finally, the generated radio frequency signals are filtered and delivered to the image reconstruction module in which the integrated signal over the entire bandwidth is synthesized and a 3-D image is formed.

Figure 6:
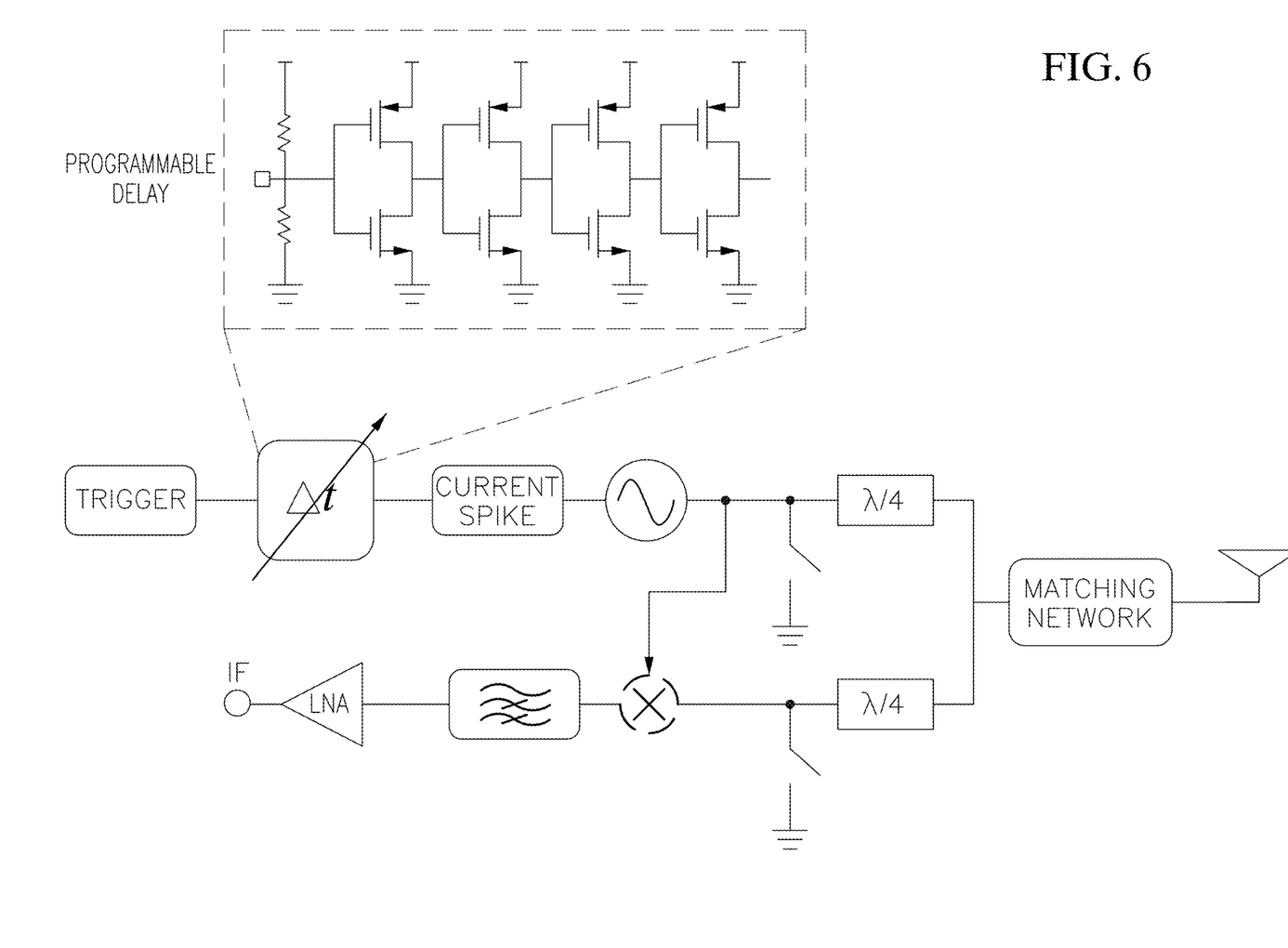
FIG. 6 is a schematic diagram of a phased-array transceiver front-end in accordance with an embodiment of the present invention.

FIG. 6 shows a schematic of a single array element, of which there will be multiple, of a proposed synthetic ultra-wideband imaging chip, in accordance with another embodiment of the present invention as described in FIG. 2. FIG. 6 demonstrates a phased-array transceiver front-end, capable of both transmit (TX) and receive (RX) operations. This is a building-block for a scalable system in which a unit cell is repeated in the X and Y directions. A digital trigger is passed through a programmable delay generator. The delay generator is a cascaded series of inverter stages controlling the timing of the digital signal using their supply voltage. The Tx and Rx sub-band antennas will have the same structure and will be integrated with the Tx and Rx frontends of the imaging circuit. In an embodiment, each sub-band transceiver element has a single combined antenna which transmits scanning signals and receives backscattered signals. Other building blocks in the front-end include a pulse generator, a multiplier, an LNA, a T/R switch, and a single on-chip antenna in silicon. The use of these specialized components, as opposed to more multi-purpose tools (e.g., Vector Network Analyzers), contributes to the goal of miniaturization. In the TX mode, the delayed input signal from the pulse generator is radiated through an antenna. A T/R switch switches the antenna between TX and RX. In the RX mode, the front-end receives the backscattered signal and mixes it with the delayed pulse generated by the pulse generator.

Figure 8:
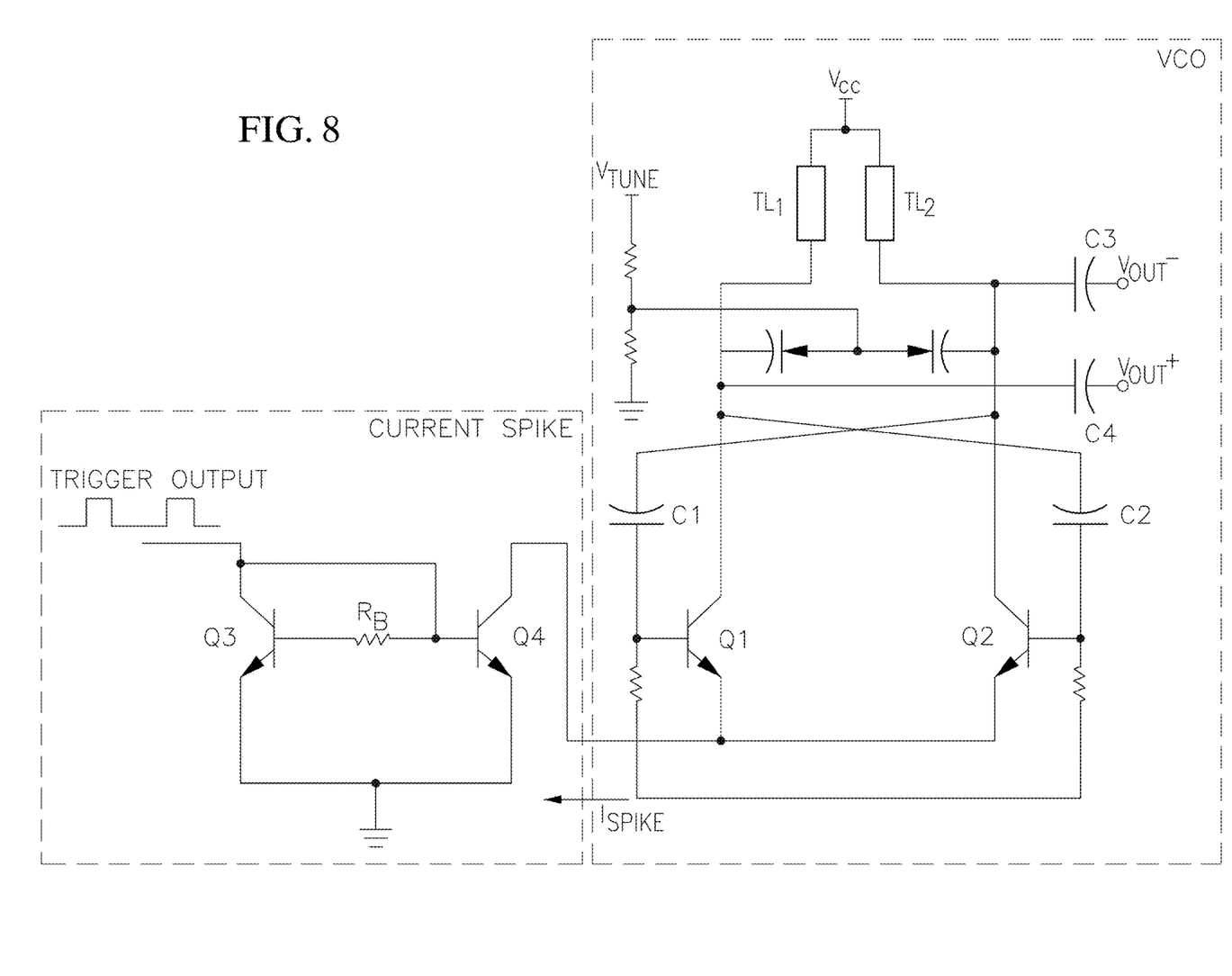
FIG. 8 is a schematic of a pulse generator adapted for use with embodiments of the present invention.

The pulse generator design will now be described. For the sake of brevity, only the topology of the first sub-band (i.e., 10-40 GHz) pulse generator will be described. Having a similar topology between the pulse generators facilitates a proper impedance match with the subsequent sub-band antennas as these antennas also need to have a similar structure to have a fixed phase center and constant transmit efficiency. FIG. 8 shows the circuit schematic of the pulse generator, comprising a current spike and a pulsed VCO with asymmetric cross-coupled topology in accordance with one embodiment. A differential topology is considered for the VCO circuit since the subsequent use of differential antennas would significantly reduce the feedline radiation. When the spike current is high enough to create a negative resistance at the collector terminals of Q1 and Q2, the VCO is turned on. A Schmitt trigger is used to feed the current spike circuit. When the trigger outputs a positive signal at the collector of Q3, the diode-connected transistor Q3 reduces this potential to the voltage set by the diode of Q3. The duration ($\tau$) of this procedure is determined by the charging circuit in the base-emitter of Q3, which can be expressed as:

$$\tau = R_B C_{BE3}$$

where $R_B$ is the resistor in the base of Q3 and $C_{BE3}$ is the base-emitter capacitor of Q3. Therefore, the collector potential of Q3 has a spike performance before becoming stable, which correspondingly generates a collector current spike at Q4.

The size of Q3 is selected to be much larger than Q4. Therefore, when the collector potential of Q3 becomes stable, the collector current of Q4 is no longer high enough to keep the VCO on. The oscillation time and accordingly the pulse frequency bandwidth are determined by the current spike width which can be controlled by $R_B$. The repetition rate of the current spike is equal to the input clock frequency. In this exemplar design, the current spike has a full width at half maximum (FWHM) of 14 ps.

Two varactors are used to apply a tuning voltage at the common anode of the VCO circuit and adjust the oscillation frequency. An impedance matching network, including differential transmission lines TL1 and TL2 and capacitors C3 and C4 provides the required inductance for resonating at the desired center frequency.

At each scanning location in the synthetic ultra-wideband approach, the three sub-band radiators need to coherently transmit their generated sub-band pulses. In addition, the sub-band pulses at different scanning locations need to be coherent as well. Both of these requirements can be fulfilled by locking the phases of all the generated pulses at all the scanning locations to a single reference signal.

This design aims to lock the phase of the generated pulses to the input trigger signal. Two following design considerations are followed in this regard: 1) the initial phase of the generated pulses should be deterministic; 2) the timing jitter added by the pulsed VCOs needs to be minimized. There are two equally-important sources of timing jitter: noise-induced perturbation during startup time and phase noise in the steady state oscillation. By making the sizes of Q1 and Q2 different, a deliberate asymmetry is introduced in the VCO structure. This results in a deterministic start-up time as well as minimizes the timing jitter.

In symmetric cross-coupled pulsed VCOs, the initial condition is introduced by thermal noise. In the asymmetric design on the other hand, the initial condition is set by the deterministic unbalanced collector current flow when the pulse VCO is switched ON. However, the unbalanced common-mode noise induced by the asymmetric pair slightly degrades phase noise in the steady state. Therefore, an optimum size ratio of the two transistors needs to be obtained for minimizing the timing jitter. Timing jitter is defined versus different length ratios of the transistors (Q2/Q1) and calculated from transient noise simulations. Two capacitors, C1 and C2, are also added to enhance the oscillation amplitude and hence reduce the phase noise.

A differential antenna, fed by two signals of equal amplitude and opposite phases, would significantly reduce the feedline radiation. As such, a broadband slot bow-tie antenna has been designed. The edges of the antenna are curved to improve the bandwidth. In designing on-chip millimeter-wave antennas, surface waves are a consideration as potentially degrading radiation efficiency. A silicon lens can be used to mitigate surface waves by collecting and converting them to useful radiation. However, attaching a silicon lens significantly increases the directivity of the on-chip antenna and limits the field-of-view. This is not a good option in applications requiring wide field-of-view imaging.

The thickness of the silicon substrate can be optimized to increase the antenna radiation efficiency. Since wire bonds may affect the topside radiation, the on-chip antennas are designed to radiate through the substrate (i.e., bottom side). Additionally, due to die area constraints, the dimensions of the antenna is up to 300 μm. With a 1500-μm silicon substrate, the on-chip sub-band bowtie antennas demonstrated 3-dB bandwidths of approximately 30 GHz, 35 GHz, and 35 GHz for the 10-40 GHz, 40-75 GHz, and 75-110 GHz sub-bands, respectively.

Further details on the design of a chip embodying the principles of present invention can be found in the publication by Amir Mirbeik-Sabzevari et al. titled "Synthetic Ultra-Wideband Integrated Pulse Generator for Millimeter-Wave Imaging Applications," 2020 18th IEEE International New Circuits and Systems Conference (NEWCAS), 2020, pp. 154-157, the entire disclosure of which is incorporated herein by reference and made part of the present disclosure for all purposes. Still further details on antenna design and related aspects embodying the principles of the present invention can be found in the publication by Amir Mirbeik-Sabzevari et al. titled "Synthetic Ultra-Wideband Phased-Array Transceiver for Millimeter-Wave Imaging Applications With On-Chip Antennas," 2021 IEEE International Symposium on Antennas and Propagation and USNC-URSI Radio Science Meeting (APS/URSI), 2021, pp. 521-522, the entire disclosure of which is incorporated herein by reference and made part of the present invention for all purposes.

Figure 7:
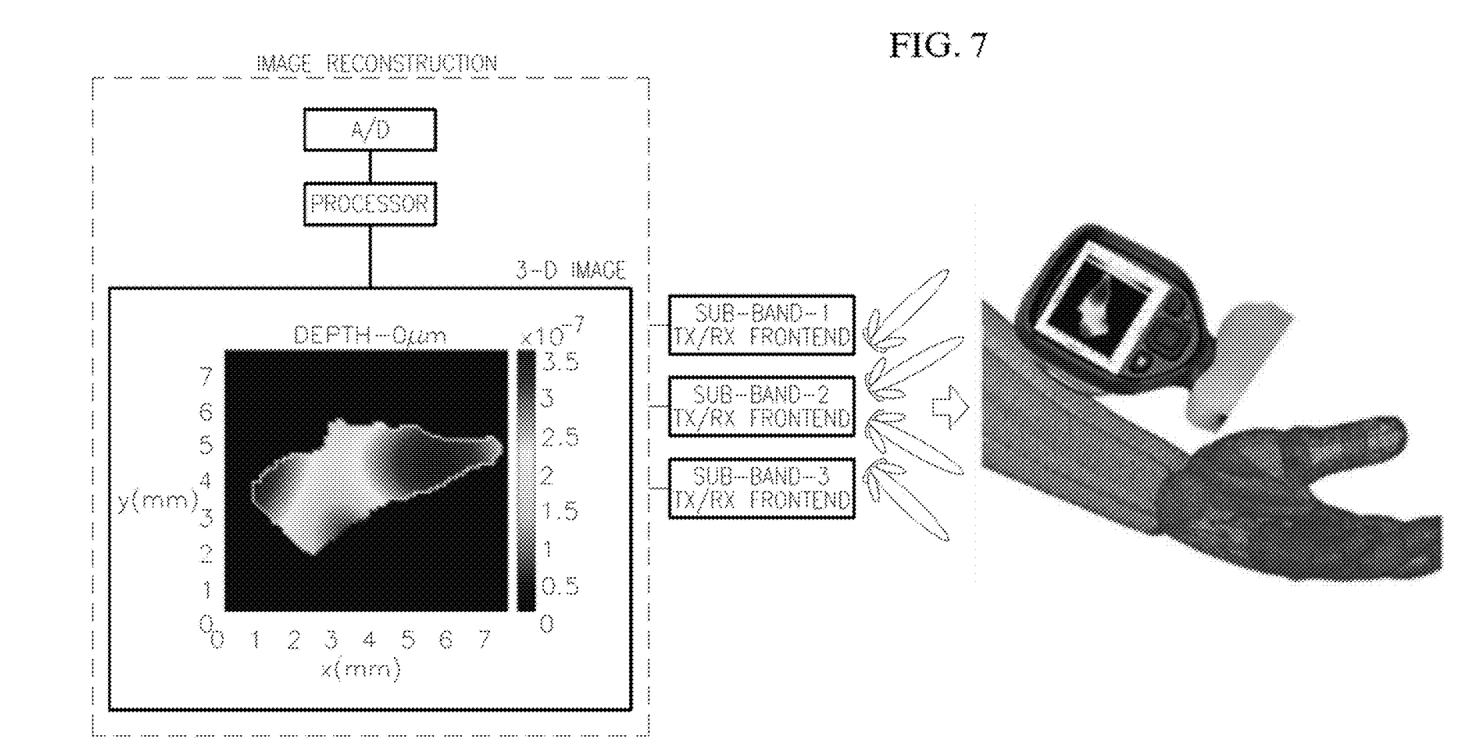
FIG. 7 is a schematic diagram, showing exemplary circuits, an imaging module and a handheld device in accordance with an embodiment of the present invention.

As a result of this present invention, a handheld probe can be developed with a significantly reduced manufacturing cost. This can be performed by integrating all the imaging sub-band antennas with their circuits on a single chip using the inventive technology. FIG. 7 shows a system diagram for a device using phased arrays for beam steering in accordance with one embodiment of the present invention. A display connected to the handheld housing and the processor, a switch connected to the processor, and a rechargeable power source connected to the handheld housing can be other components of the device.

Further embodiments and details of the present invention are presented in abandoned U.S. Provisional Patent Application Ser. No. 62/805,246, which application is incorporated herein by reference and made a part of the present application for all purposes.

Additional details are also presented in the publication by Amir Mirbeik-Sabzevari et al., titled "Ultra-Wideband Millimeter-Wave Dielectric Characteristics of Freshly Excised Normal and Malignant Human Skin Tissues," *IEEE Transactions on Biomedical Engineering*, Vol. 65, No. 6, June 2018, pp. 1320-1329, <URL: https://ieeexplore.ieee.org/document/8026147> <DOI: 10.1109/TBME.2017.2749371>, in the publication by Amir Mirbeik-Sabzevari et al., titled "Synthetic Ultra-High-Resolution Millimeter-Wave Imaging for Skin Cancer Detection," *IEEE Transactions on Biomedical Engineering*, Vol. 66, No. 1, January 2019, pp. 61-71, <URL: https://ieeexplore.ieee.org/abstract/document/8360774> <DOI: 10.1109/TBME.2018.2837102>, in the publication by Amir Mirbeik-Sabzevari et al., titled "W-Band Micromachined Antipodal Vivaldi Antenna Using SIW and CPW Structures," *IEEE Transactions on Antennas and Propagation*, Vol. 66, No. 11, November 2018, pp. 6352-6357, <URL: https://ieeexplore.ieee.org/document/8425012> <DOI: 10.1109/TAP.2018.2863098>, and in the publication by Amir Mirbeik-Sabzevari et al., titled "Characterization and Validation of the Slim-Form Open-Ended Coaxial Probe for the Dielectric Characterization of Biological Tissues at Millimeter-Wave Frequencies," *IEEE Microwave and Wireless Components Letters*, Vol. 28, No. 1, January 2018, pp. 85-87, <URL: https://ieeexplore.ieee.org/document/8123612> <DOI: 10.1109/LMWC.2017.2772187>. The entire disclosures of each of the foregoing publications are incorporated herein by reference and made part of the present disclosure.

It will be understood that the embodiments described herein are merely exemplary and that a person skilled in the art may make many variations and modifications without departing from the spirit and scope of the invention. All such variations and modifications are intended to be included within the scope of the invention, as defined by the appended claims.

We claim:

1. A method for imaging tissue, said method comprising the steps of:
    transmitting, from each of a plurality of sub-band imaging elements to a targeted tissue, output signals operating in a corresponding one of a plurality of predetermined sub-bands of a range of millimeter-wave frequencies, wherein each sub-band imaging element of the plurality of sub-band imaging elements is configured to operate only in its corresponding sub-band which is different from the sub-band of each and every other one of the plurality of sub-band imaging elements;
    scanning the targeted tissue using electronic beam-forming;
    controlling, via a respective programmable delay or phase shifter line for each sub-band imaging element of the plurality of sub-band imaging elements, individual timing of radiation for electronic beam-forming to perform low-loss signal distribution and coherent combination of broadband pulses of associated elements;
    receiving, at each sub-band imaging element, respective return signals reflected from the targeted tissue in response to the performance of the transmitting step for each of the plurality of sub-band imaging elements;
    wherein the transmitting and receiving steps are performed sequentially as a cycle for each sub-band imaging element of the plurality of sub-band imaging elements at each of a plurality of scanning locations;
    wherein each sub-band imaging element of the plurality of sub-band imaging elements is sequentially positioned at a distinct position in each of the plurality of scanning locations for the performance of the transmitting and receiving steps;
    combining, at a processor, said respective return signals to form an integrated signal covering the range of millimeter-wave frequencies; and
    using the integrated signal to generate an image of the targeted tissue.

2. The method of claim 1, wherein said transmitting step comprises the step of scanning transmitting and receiving elements of each of said plurality of sub-band imaging elements over a rectilinear planar aperture.

3. The method of claim 1, wherein said transmitting step comprises the step of selectively switching on and off individual antennae of an array of antennae corresponding to a sub-band imaging element using a switching network, wherein each sub-band imaging element comprises a combined transmitting and receiving antenna and a pulse generator.

4. The method of claim 1, wherein the step of using the integrated signal to generate an image of the targeted tissue includes calculating pulse responses from incident pulses in frequency domain by using the integrated signal.

5. The method of claim 4, wherein the step of using the integrated signal to generate an image of the targeted tissue includes converting the pulse responses to time domain by using an Inverse Fourier Transform operation.

6. The method of claim 5, wherein the step of using the integrated signal to generate an image of the targeted tissue includes applying a reconstruction algorithm to the pulse responses to generate the image of the targeted tissue.

7. The method of claim 4, wherein said processor uses the integrated signal as a transfer function to calculate said pulse responses from said incident pulses in the frequency domain.

8. The method of claim 1, wherein said sub-band imaging elements are integrated on a single chip.

9. The method of claim 1, further comprising the steps of amplifying the respective return signals; and mixing said amplified respective return signals with corresponding transmitted signals using a respective sub-band mixer for each of the sub-band imaging elements prior to said combining step.

10. A device for imaging tissue, comprising:
    an imaging element configured to transmit and receive signals operating in a range of millimeter-wave frequencies,
    wherein the range of millimeter-wave frequencies are divided into a plurality of predetermined sub-bands,
    wherein the imaging element includes a plurality of sub-band imaging elements comprising a plurality of radiators including a pulse generator and an antenna, said sub-band imaging elements being configured to transmit signals to a targeted tissue and to receive signals reflected from the targeted tissue,
    wherein said sub-band imaging elements are configured to scan the targeted tissue using electronic beam-forming, and wherein each sub-band imaging element comprises a respective programmable delay or phase shifter line that controls the individual timing of radiation to perform low-loss signal distribution and coherent combination of broadband pulses of associated elements,
    wherein each of said plurality of predetermined sub-bands is assigned to one of said plurality of sub-band imaging elements such that each of said plurality of sub-band imaging elements is configured to transmit to the targeted tissue signals operating in a corresponding one of said plurality of predetermined sub-bands, wherein each of the plurality of sub-band imaging elements is configured to operate only in its corresponding sub-band which is different from the sub-band assigned to each and every other one of the plurality of sub-band imaging elements;

wherein each sub-band imaging element of the plurality of sub-band imaging elements is configured to be sequentially positioned at a distinct scanning position in each of a plurality of scanning locations, wherein the plurality of sub-band imaging elements is configured so as to transmit, sequentially from each of said plurality of sub-band imaging elements in each of said scanning locations, output signals operating in a corresponding one of the plurality of predetermined sub-bands, and to receive, at one or more of the plurality of sub-band imaging elements, return signals reflected from the targeted tissue;

wherein each sub-band imaging element comprises a combined transmitting and receiving antenna and a pulse generator; and a processor connected to the sub-band imaging elements, the processor configured to receive and combine the return signals so as to form an integrated signal covering the preset range of millimeter-wave frequencies, whereby the integrated signal is used to generate an image of the targeted tissue.

11. The device of claim 10, wherein said processor is configured to calculate pulse responses from incident pulses in frequency domain by using the integrated signal.

12. The device of claim 11, wherein said processor is configured to convert the pulse responses to time domain by using an Inverse Fourier Transform operation.

13. The device of claim 12, wherein said processor is configured to apply a reconstruction algorithm to the pulse responses to generate the image of the targeted tissue.

14. The device of claim 10, wherein said sub-band imaging elements are configured to scan said targeted tissue through a rectilinear planar aperture.

15. The device of claim 10, further comprising a switching network configured to selectively switch on and off individual antennae of an array of antennae corresponding to a sub-band imaging element.

16. The device of claim 10, wherein said processor is configured to use the integrated signal to generate the image of the targeted tissue by calculating pulse responses from incident pulses in frequency domain.

17. The device of claim 10, wherein said sub-band imaging elements are integrated on a single chip.

18. The device of claim 10, wherein said sub-band imaging elements are configured to scan the targeted tissue using Frequency-Modulated Continuous Wave imaging.

19. The device of claim 10, wherein said sub-band imaging elements are configured to scan the targeted tissue using a Synthetic Aperture Radar technique.

20. The device of claim 10, further comprising a plurality of voltage-controlled oscillators configured to produce said transmitted signals.

21. The device of claim 10, wherein each sub-band imaging element further comprises a sub-band mixer adapted to receive respective amplified return signals and combine the amplified return signals with corresponding transmitted signals to create mixed signals.

* * * * *